United States Patent [19]

Cunniff

[11] Patent Number: 5,474,084
[45] Date of Patent: Dec. 12, 1995

[54] ALGESIMETER WITH DETACHABLE PIN WHEEL

[76] Inventor: Joseph G. Cunniff, 6450 Wisconsin Ave., Chevy Chase, Md. 20815

[21] Appl. No.: 213,428

[22] Filed: Mar. 15, 1994

[51] Int. Cl.⁶ ................................................ A61B 19/00
[52] U.S. Cl. ............................................................ 128/744
[58] Field of Search .................................. 128/744, 740, 128/774; 601/128, 129; 606/181

[56] References Cited

U.S. PATENT DOCUMENTS

| | | |
|---|---|---|
| 3,074,395 | 1/1963 | Kevorkian . |
| 3,344,781 | 10/1967 | Allen . |
| 3,515,125 | 6/1970 | Ruskin ................................ 128/744 |
| 4,823,806 | 4/1989 | Bajada ................................ 128/744 |
| 5,222,504 | 6/1993 | Solomon ............................. 128/744 |
| 5,316,012 | 5/1994 | Siegal ................................. 128/744 |

*Primary Examiner*—Max Hindenburg
*Attorney, Agent, or Firm*—Lowe, Price, LeBlanc & Becker

[57] ABSTRACT

An algesimeter which includes a pin wheel that is disposable and easily attachable/detachable to a handle structure. The algesimeter includes a handle, a pair of pivotable arm members extending from the handle, and a pin wheel releasably held between the pair of pivotable arm members. A release mechanism is provided within the handle for pivoting the arm members between an open and closed position, wherein the pin wheel is rotatably held by the pair of arm members in the closed position and released from the pair of arm members in the open position. A pin wheel can be attached and/or released from the handle without being directly contacted by the user.

17 Claims, 4 Drawing Sheets

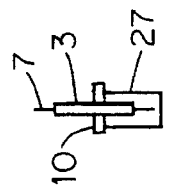
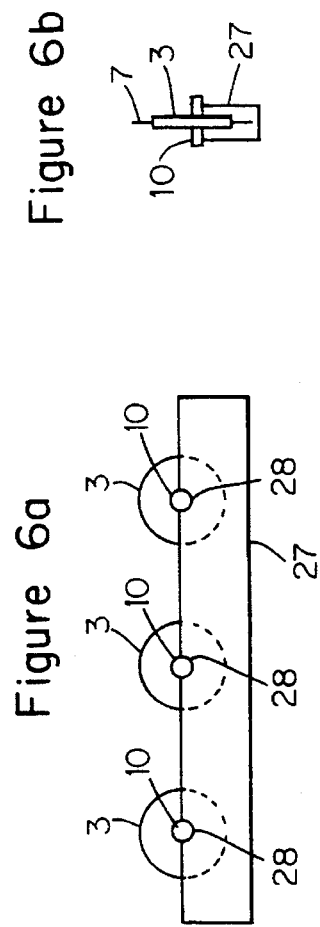
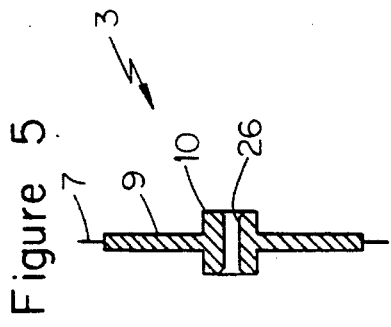
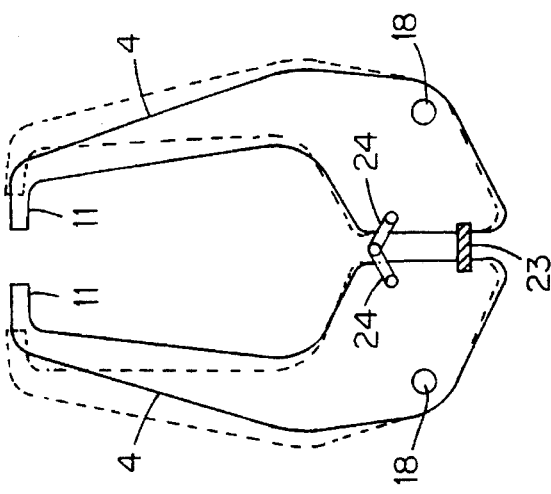
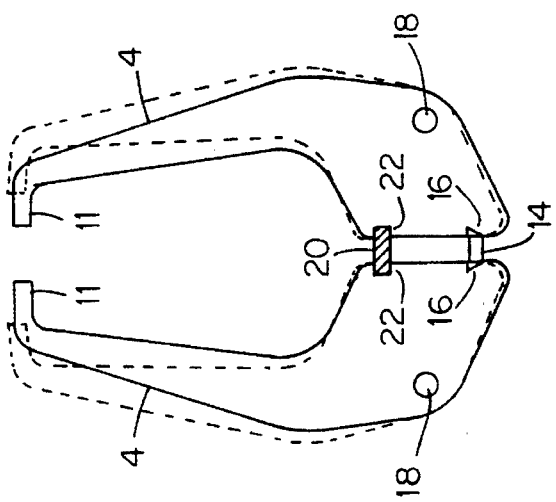
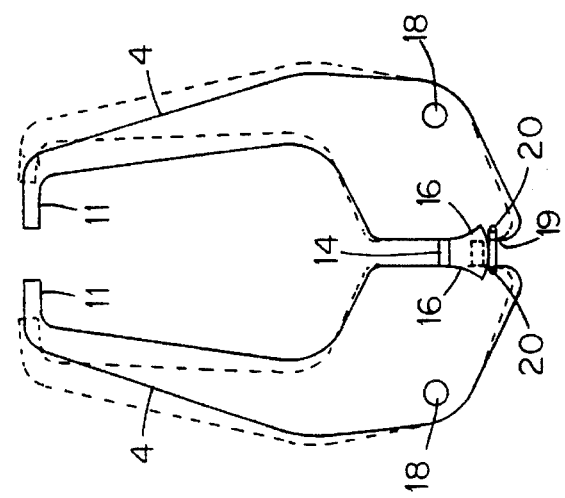

ALGESIMETER WITH DETACHABLE PIN WHEEL

TECHNICAL FIELD

The present invention relates to neurological diagnostic tools. More particularly, the present invention relates to an algesimeter which includes a pin wheel that is disposable and easily attachable/detachable to a handle structure.

BACKGROUND ART

In neurological and other medical examinations, it is often necessary to locate and outline areas of analgesia, or no-pain sensitivity, as well as areas of hypesthesia, or reduced pain sensitivity, of the skin of a patient. Such mapping procedures are necessary in cases of special examinations for the purpose of treatment of neurological disorders as well as in general medical checkups, in diagnosing other diseases, and in the testing the effects of local anesthesia.

Such mapping procedures can be performed by lightly striking the skin of a patient with a pin, while the patient reports on the degree of pain felt. If areas of no-pain sensitivity or of reduced sensitivity are located, more strikes with the pin are made in the general vicinity in order to determine the boundary of the affected area and to outline or map the same.

It can be appreciated that the closer such pin strikes are made, the more precise is the location of the affected areas. In addition, the more uniform the force of the pin strikes, the more reliable are the results.

If such a mapping procedure is conducted on large areas of the skin or over the entire body of a patient, the number of the required pin strikes may be exceedingly large and the overall procedure may take an exceedingly long time.

While examination of large relatively flat portions of the body may be facilitated by the use of an instrument in the form of a pin brush, the use of single pins is still required over many body areas, and a full examination can take several days.

It has also been found that muscular coordination of the medical examiner required to make pin strikes with the requisite uniformity is exceedingly difficult to attain except for persons at the height of their muscular coordination, and is often unattainable for an older practitioner. Therefore, in many cases, the differences in the pain sensitivity reported by the patient may be due not to the causes determined by the health condition of the patient, but by the variance in the intensity of the pin strikes made by the medical examiner. Thus, in some cases the variance in pain felt by the patient may be the test not of pain sensitivity of the skin but, in effect, of the muscular coordination of the medical examiner. Results of such tests are obviously unreliable for the purposes of medical diagnosis and treatment.

In order to overcome the disadvantages associated with pin striking procedures, a device which includes a rotatable wheel with sharp prongs mounted on the periphery of the wheel has been developed and widely accepted. The pin wheel which is rotatably mounted on a handle is conveniently rolled over the skin of a patient during a mapping procedure.

U.S. Pat. No 3,344,781 to Allen discloses a multi-purpose neurological diagnostic instrument which includes a pin wheel "C" in addition to other diagnostic devices.

U.S. Pat. No. 3,074,395 to Kevorkian discloses an algesimeter which includes a pin wheel 23 that is connected to a yielding mechanism. The yielding mechanism regulates the force applied to the pin wheel.

German patent No. 2,319,591 discloses a surgical needle roller which is releasable mounted in a holder for quick sterilizing. As illustrated in FIG. 4, a roller is secured at opposite ends to holder 1 by biasing springs.

German patent No. 3,245,286 discloses a skin and muscle massage treatment apparatus which includes two exchangeable rollers with rigid projections that are located in frame 1.

Currently, pin wheel algesimeters are designed to be reusable and thus, may be sterilized for each use. German patent No. 2,319,591 is an example of a algesimeter design which is particularly designed for sterilization of the roller.

With the present concern for diseases such as AIDS which are spread by blood-contaminated articles, there is considerable anxiety associated with devices that are intended to prick or puncture a subject's skin when used.

The present invention provides an algesimeter which has a disposable pin wheel that can be easily attachable/detachable to a handle structure.

DISCLOSURE OF THE INVENTION

It is accordingly one object of the present invention to provide an algesimeter.

Another object of the present invention is to provide an algesimeter which includes a disposable pin wheel.

A further object of the present invention is to provide an algesimeter which includes an attachable/detachable pin wheel.

A further object of the present invention is to provide an algesimeter which has a pin wheel that can be attached and detached from a handle without the user having to touch the pin wheel.

A still further object of the present invention is to provide an algesimeter with a disposable pin wheel that can be attached and detached from a handle without the user having to touch the pin wheel.

A still further object of the present invention is to provide packaged pin wheels which can be attached to a handle without having to be contacted by the user.

According to these and further objects of the present invention which will become apparent as the description thereof proceeds, the present invention provides a device for testing the pain sensitivity of the skin of a patient which includes a handle;

a pair of pivotable arm members extending from the handle;

a pin wheel releasably held between the pair of pivotable arm members; and a release mechanism within the handle for pivoting the arm members between an open and closed position, wherein the pin wheel is rotatably held by the pair of arm members in the closed position and released from the pair of arm members in the open position.

The present invention further provides for a method of testing the pain sensitivity of the skin of a patient which involves:

providing a handle having a a pair of pivotable arm members extending from the handle, the pair of pivotable arm members including opposed axial portions, and a release mechanism within the handle for pivoting the arm members between an open and closed position, wherein the pin wheel is rotatably held by the pair of arm members in the closed position and released from the pair of arm members in the open position;

providing at least one pin wheel having a central hub with a through-bore extending through the hub;

moving the pair of pivotable arms into the open position and aligning the opposed axial portions with the through-bore in the pin wheel hub;

moving the pair of arm members into the closed position so that the opposed axial portions are received in the through-bore in the pin wheel hub to rotatably hold the pin wheel; and rolling the pin wheel across the skin of a patient to test pain sensitivity of the skin of the patient.

BRIEF DESCRIPTION OF DRAWINGS

The present invention will be described with reference to the annexed drawings which are given by way of non-limiting examples only, in which

FIGS. 4a–4c are top views of the pin wheel release mechanisms of different embodiments of the present invention.

FIG. 5 is a cross sectional view of the pin wheel which depicts the structure of the pin wheel hub according to one embodiment of the present invention.

FIG. 6a is a side view of a pin wheel holder according to one embodiment of the present invention.

FIG. 6b is an end view of the pin wheel holder of FIG. 6a.

BEST MODE FOR CARRYING OUT THE INVENTION

The present invention is directed to an algesimeter which includes a handle and a rotatable pin wheel which is attachable/detachable to the handle. The algesimeter is designed to be utilized with a disposable pin wheel or a pin wheel which can be removed for sterilization between each use. The algesimeter includes a pin wheel release mechanism which the operator can manipulate to easily attach and/or remove a pin wheel from the handle without having to touch the pin wheel.

Figure 7:
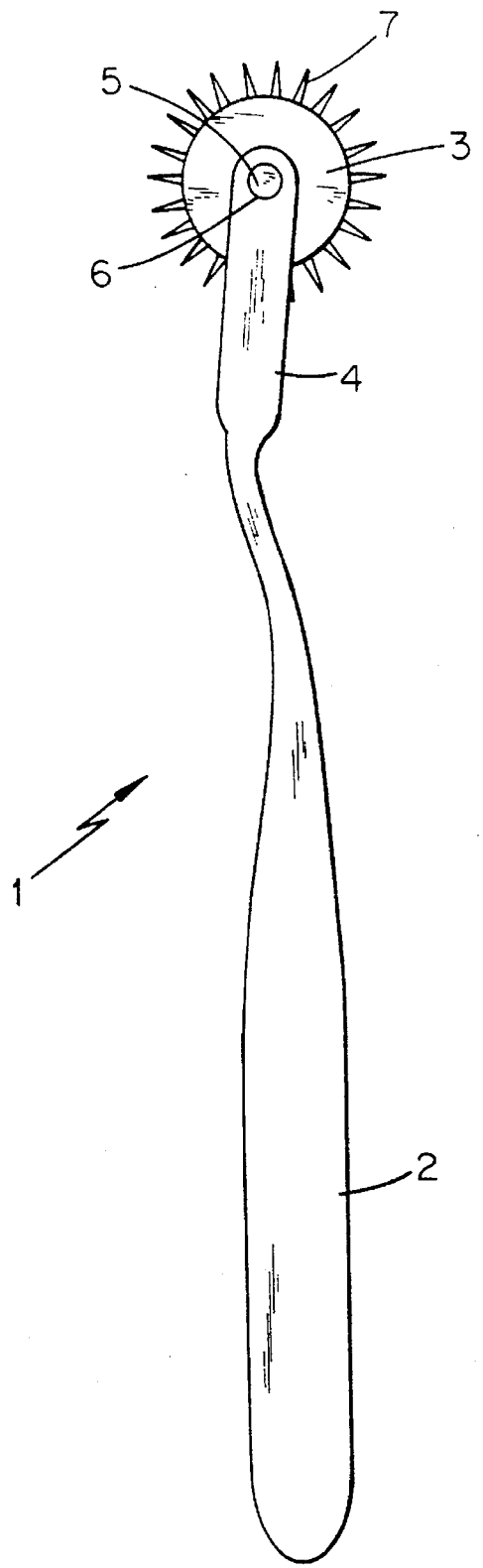
FIG. 7 is a side view of a prior art algesimeter.

FIG. 7 is a side view of a prior art algesimeter. The prior art algesimeter 1 includes a handle 2 and a pin wheel 3 which is secured between a pair of arms 4 by a shaft 5 which passes through the center of the pin wheel 3 and is secured in bores 6 in the arms 4. The pin wheel 3 includes a plurality of pins 7 which are evenly spaced about the periphery of the pin wheel 3 as shown.

In the prior art algesimeter 1 of FIG. 7, the pin wheel 3 is permanently attached to the handle 2. Accordingly, the entire structure is made from a metal such as stainless steel so that the algesimeter 1 can be sterilized.

Before referring to the figures which depict applicant's invention it is noted that in all the figures, the same reference numerals have been used for similar elements. However, it is to be understood that this use of common reference numerals is for convenience and descriptive purposes only and is not an admission that the prior art elements are used in the present invention, except where explicitly stated. It is also to be understood that the drawings are for illustration purposes only and are therefore not drawn to scale.

Figure 1B:
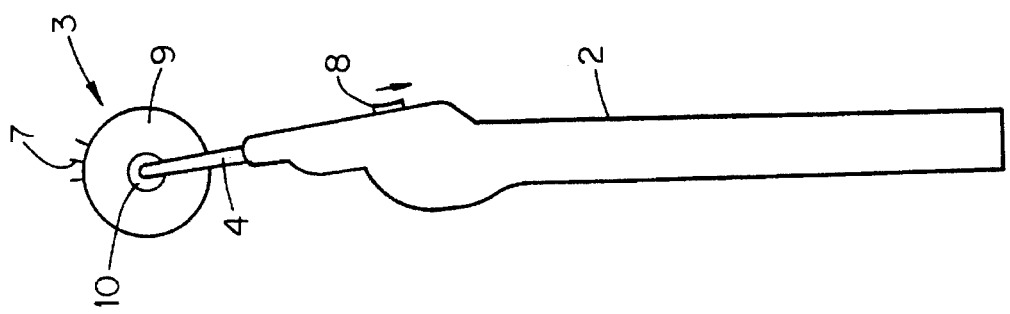
FIG. 1a and 1b are side views of algesimeters according to different embodiments of the present invention.
Figure 1A:
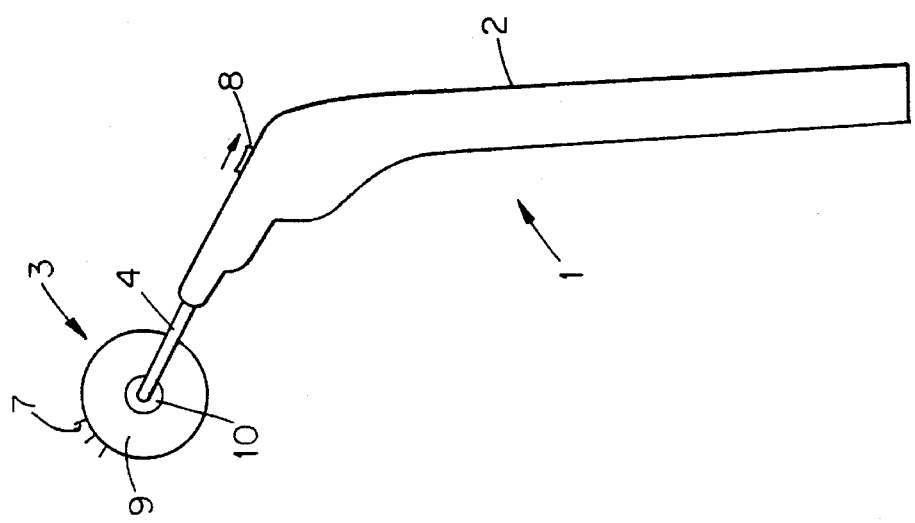

FIG. 1a is a side view of an algesimeter according to the present invention. The algesimeter 1 includes a pin wheel 3 which is supported by a pair of pivotable arm members 4. The pivotable arm members 4 are connected to a pin wheel release mechanism, discussed in detail below, which is located within the handle 2. A pin wheel release lever 8 is shown in FIG. 1a. The pin wheel release lever 8 is slidable between a first position in which the pin wheel release mechanism pivots the pair of arm members 4 into a closed position to securely hold the pin wheel 3 and a second position in which the pin wheel release mechanism pivots the pair of arm members 4 into a open position in which the pin wheel 3 can be removed from the algesimeter 1.

In FIG. 1a the pin wheel 3 includes a plurality of pins 7 which extend from the periphery of the wheel portion 9. The plurality of pins 7 are evenly spaced about the periphery of the wheel 9 (only a few pins 7 are shown), preferable in a single roll.

The algesimeter 1 shown in FIG. 1b is similar to the algesimeter 1 shown in FIG. 1a except the overall shape of the handle 2. The handle 2 in FIG. 1a is configured so that the center of the pin wheel 3 is substantially aligned with the axis of the lower portion of the handle 2. The alignment of the pin wheel 3 and handle 2 in this embodiment is similar to the prior art algesimeter 1 of FIG. 5.

Figure 2:
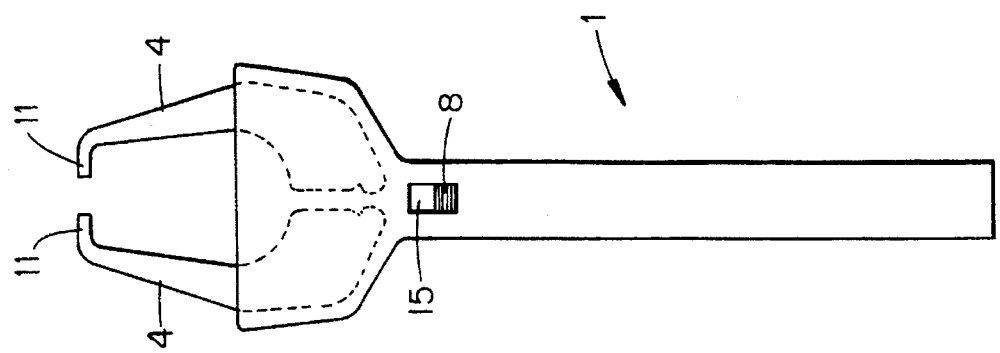
FIG. 2 is a back view of the algesimeter of FIG. 1b.

FIG. 2 is a back view of the algesimeter 1 of FIG. 1a 1b (viewed from the right). In FIG. 2 the arm members 4 are shown in their closed position. In this position, the hub 10 of the pin wheel 3 would normally receive the axis portions 11 of the arm members 4 so as to rotatably secure the pin wheel 3 (not shown in FIG. 2). The arm members 4 are held within an upper portion of the handle 2 as shown. Also shown in FIG. 2 is the pin wheel release lever 8. The pin wheel release lever 8 is preferably located on the back of the handle 2 so that it can be easily slid between the first and second position by the operator's thumb.

In FIGS. 1a–1b and 2 the lower portion handle 2 is shown as having a generally cylindrical shape. In an alterative embodiment, the lower portion of the handle can be configured with a comfortable gripping shape.

Figure 3A:
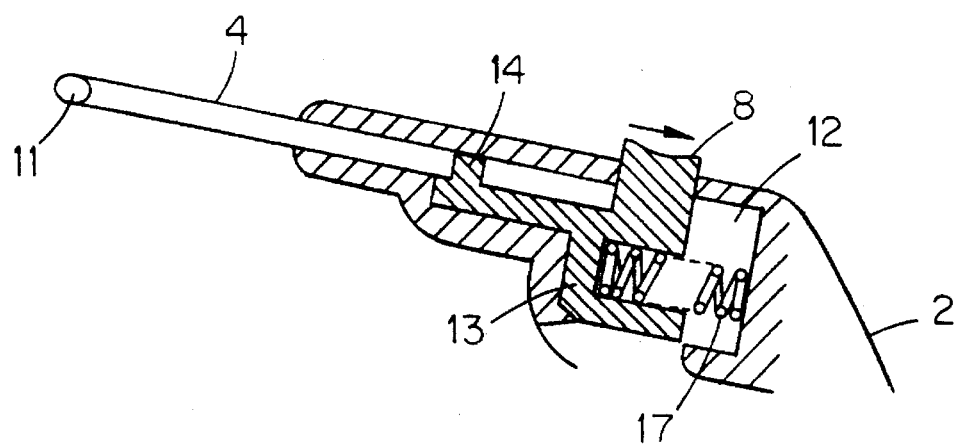
FIGS. 3a and 3b are planar views of the pin wheel release mechanisms of different embodiments of the present invention.
Figure 3B:
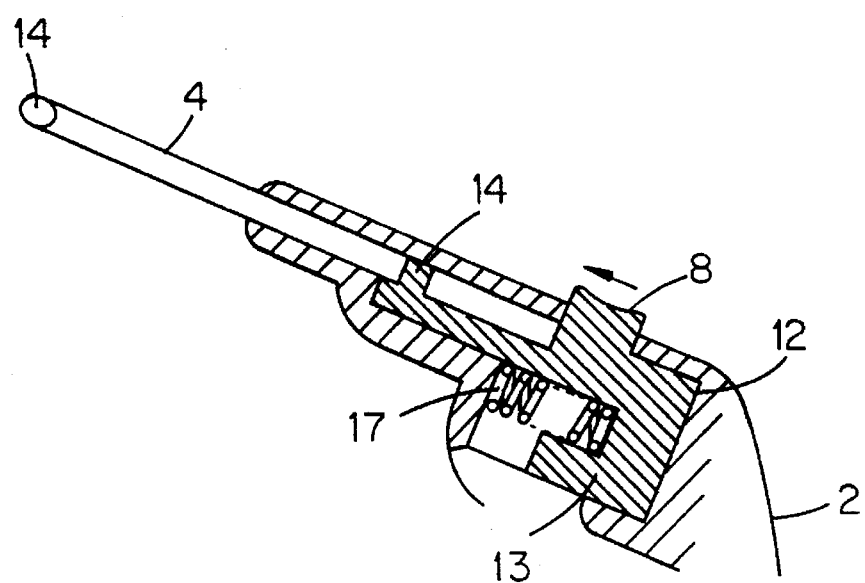

FIGS. 3a and 3b are planar views of the pin wheel release mechanisms of different embodiments of the present invention. In FIG. 3a the pin wheel release mechanism is shown as being within a chamber 12 in the upper portion of the handle 2. The pin wheel release mechanism includes a sliding member 13. A cam projection 14 extends from an upper surface of the sliding member 13. The pin wheel release lever 8 also extends from an upper surface of the of the sliding member 13. As shown in FIGS. 3a and 3b, the cam projection 14 does not extend outside chamber 12. However, the pin wheel release lever 8 does extend through a slot 15 (FIG. 2) in the upper surface of the handle 2 so as to be engageable by the operator. As shown, the pin release lever 8 preferably has a slightly concave upper surface for receiving an operator's thumb. The upper surface of the pin release lever 8 can also be roughened, grooved, etc., to provide more friction for engaging.

The cam projection 14 engages cam surfaces 16 of the arm members 4 as discussed in more detail below. In operation, sliding the pin wheel release lever 8 in slot 15 causes the cam projection 14 to move between a first and second position. This movement of the cam projection 14 causes the arm members 4 to pivot between open and closed positions as discussed below.

Although the sliding member 13 is designed to slide when the pin wheel release lever 8 is engaged and slid, the sliding member 13 is normally held in a remote position by a spring member 17 which applies a biasing force on the sliding member 13.

In FIG. 3a the spring member 17 urges the sliding member 13 in the direction of the arm members 4. In the embodiment of the invention shown in FIG. 3b the spring member 17 urges the sliding member 13 in the direction of the handle 2. The spring member 17 preferably urges the sliding member 13 in a remote position which causes the arm members 4 to be closed so that the tendency of the pin wheel release mechanism is to secure a pin wheel between arm members 4. Thus, when the pin wheel release lever 8 is slid against the biasing force of the spring member 17 the arm members 4 open and release or receive a pin wheel. When the pin wheel release lever 8 is released by the operator, the biasing force of the spring member 17, operating through the pin release mechanism causes the arm members 4 to close and secure a pin wheel 3 between the arm members 4. As will be explained below, according to different embodiments of the present invention, the arm members 4 can be either opened or closed as the sliding member 13 moves from one remote position to the other.

FIGS. 4a–4c are top views of the pin wheel release mechanisms of different embodiments of the present invention.

In FIG. 4a the arm members 4 are shown in their open position (in phantom lines) and a closed position (solid lines) In the open position, the axis portions 11 of the arm members 4 are sufficiently spaced apart so that a pin wheel can be removed or received from the arm members 4. In their closed position, the axis portions 11 of the arm members 4 engage and secure a rotatable pin wheel 3. A description of the pin wheel will be discussed below.

The arm members 4 are provided with opposed cam surfaces 16 and pivot points 18. The pivot points 18 can include through holes in the arm members 4 which receive corresponding posts within the chamber 12 of the handle 2. According to another embodiment, the pivot points 18 can include post members formed on one or both surfaces of the arm members 4 are corresponding bores which receive the post members in the chamber 12 of the handle 2.

In FIG. 4a a biasing element 19 is shown as being connected between the arm members 4 below the opposed cam surfaces 16. The biasing element 19 can comprise a spring, a strip of an elastic material, an o-ring made from an elastic material, or any similar means which pulls the lower opposed portions of the arm members 4 toward each other. FIG. 4a illustrates a mechanical means 20, e.g. posts, screws, or similar means which secure the biasing element between the arm members 4.

The cam projection 14 is shown in FIG. 4a. As can be understood, when the cam projection 14 is moved in the forward position (upper position or solid line depiction) in FIG. 4a, the arm members 4 are urged in their closed position by the biasing element 19, due to the manner in which the arm members 4 pivot about the pivot points 18 as the cam projection 14 moves along the opposed cam surfaces 16. As the cam projection 14 is moved in the rearward position (lower position or phantom depiction) in FIG. 4a, the arm members 4 are urged in their open position as the cam projection 14 moves along the opposed cam surfaces 16 and the biasing element 19 pulls the lower portions of the arm members 4 together (as they pivot about the pivot points 18).

As indicated above, the cam projection 14 is moved as the operator engages and slides the pin wheel release lever 8 along slot 15. The embodiment of the invention depicted in FIG. 4a corresponds to the embodiment of the pin wheel release mechanism depicted in FIG. 3a. That is, in FIG. 3a the spring member 17 biases the sliding member 13 and hence the cam projection 14 in the forward position, which is corresponds to the closed position of the arm members 4 in FIG. 4a. Because the pin release mechanism, including the spring member 17, cam projection 14, etc. causes the arm members 4 to normally be in their closed position, a pin wheel 3 can be rotatably secured to the handle 2 without the operator having to manipulate the device.

FIG. 4a depicts another embodiment of the pin release mechanism of the present invention. In FIG. 4b a biasing member 21 is positioned between the opposed surfaces of the lower portion of the arm members 4 above the cam surface 16. In FIG. 4b, the opposed cam surfaces 16 of the arm members 4 are reversed from the opposed cam surfaces 16 shown in FIG. 4a. Accordingly, in FIG. 4b it can be understood that as the cam projection 14 moves to the forward or upper position in FIG. 4b, the arm members 4 are pivoted into their open position by the force of the biasing member 21. As the cam projection 14 moves to the rearward or lower position in FIG. 4b, the arm members 4 are pivoted into their closed position as the cam projection 14 coacts with the opposed cam surfaces 16 and causes the arm members 4 to pivot against the biasing force of the biasing member 21.

The biasing member 21 can be a solid block of a resilient material, such as rubber, a spring, or the like, and can be received an indent 22 formed in the arm The embodiment of the invention depicted in FIG. 4b corresponds to the embodiment of the pin wheel release mechanism depicted in FIG. 3b. That is, in FIG. 3b the spring member 17 biases the sliding member 13 and hence the cam projection 14 in the rearward position, which corresponds to the closed position of the arm members 4 in FIG. 4b. Because the pin release mechanism, including the spring member 17, cam projection 14, etc. causes the arm members 4 to normally be in their closed position, a pin wheel 3 can be rotatably secured to the handle 2 without the operator having to manipulate the device.

FIG. 4c depicts another embodiment of the pin release mechanism of the present invention. In FIG. 4c a biasing member 23 is positioned between the opposed surfaces of the lower portion of the arm members 4. There are no cam surfaces in this embodiment of the invention. Instead, a pair of pivotable link elements 24 are linked together and pivotally secured to opposed surfaces of the lower portion of the arm members 4 above the biasing member 23. The center portion where the link elements 24 are connected is connected to the cam projection 14, which can be reduced to a pin or post structure in this embodiment of the present invention. In operation, as the cam projection 14 is moved in the forward or upper position in FIG. 4b, the arm members 4 are pivoted into their closed position by the force of the biasing member 23. As the cam projection 14 moves to the rearward or lower position in FIG. 4b, the arm members 4 are pivoted into their open position as the cam projection 14 pulls the link elements 24 so that the angle formed between the link elements 24 increases and causes the arm members 4 to pivot against the biasing force of the biasing member 23.

The biasing member 23 can be a solid block of a resilient material, such as rubber, a spring, or the like, and can be received in an indent 25 formed in the arm members as shown.

The embodiment of the invention depicted in FIG. 4c corresponds to the embodiment of the pin wheel release mechanism depicted in FIG. 3b. That is, in FIG. 3a the spring member 17 biases the sliding member 13 and hence the cam projection 14 in the rearward position, which corresponds to the closed position of the arm members 4 in FIG. 4c. Because the pin release mechanism, including the spring member 17, cam projection 14, etc. causes the arm members 4 to normally be in their closed position, a pin wheel 3 can be rotatably secured to the handle 2 without the operator having to manipulate the device.

FIG. 5 is a cross sectional view of the pin wheel which depicts the structure of the pin wheel hub 10 according to one embodiment of the present invention. As can be seen from FIG. 5, the pin wheel 3 includes a circular wheel 9 (see FIGS. 1a and 1b) having a plurality of pins 7 which extend outward from the periphery of the wheel 9. A hub 10 is provided at the center of the wheel 9. A through-bore 26 extends through both the hub 10 and wheel 9. The through-bore 26 has an inner diameter which is equal to or slightly larger than the outside diameter of the axial portions 11 of the arm members 4. In use, the through-bore 26 receives the axial portions 11 of the arm members 4 and supports the pin wheel 3 so that the pin wheel 3 can freely rotate between the arm members 4. In a preferred embodiment, the edges of the through-bore 26 are beveled or slightly tapered as shown so as to assist in the alignment of the axial portions 111 of the arm members 4 when a pin wheel 3 is to be attached to the algesimeter. In an alterative, the hub can be provided with aligned stepped-bores on opposite sides thereof rather than a through-bore.

The wheel 9, hub 10, and pins 7 are preferably integral with one another. These elements of the pin wheel 3 can be made of a sterilizable material, such as surgical or stainless steel, a chrome-plated metal, or the like. If the pin wheel 3 is to be disposable after a single use, the elements of the pin wheel 3 can be made from rigid plastic material such as polycarbonate, polyethylene, etc.

The arm members 4 of the device of the present invention are preferably made from a non-corrodible metal which can be sterilized by wiping with a sterilizing solution. Preferably, the arm members 4 are made from surgical or stainless steel, a chrome plated metal, or the like. The handle 2 can be made of a suitable rigid plastic such as polycarbonate, polyethylene, or the like. The sliding member 13 of the pin wheel release mechanism shown in FIGS. 3a and 3b can be made of a rigid moldable plastic. The various springs elements mentioned above can be made from a non-corrosive metal such as stainless or spring steel.

In operation, the operator grips the handle portion of the algesimeter and manipulates the pin release lever with his or her thumb. The pin release lever is manipulated or slid by the operator to cause the arm members to move in their open position as discussed above. With the arm members held by the operator in the open position, the operator aligns the axial portions of the arm members with the through-bore of a pin wheel. Once the axial portions of the arm members are properly aligned with the through-bore of a pin wheel, the operator can release the pin wheel release lever. Once the pin wheel release lever is released the pin wheel release mechanism causes the arm members to move in their closed position in which the axial portions of the arm members engage the through-bore of the pin wheel.

To release the pin wheel, the operator need only manipulate or slide the pin wheel release lever to cause the arm members to move in their open position. With the arm members in their open position the pin wheel can be easily pushed off the axial portions of the arm members.

One advantage of the present invention is that the pin wheels can be attached, used and detached from the handle without being touched by the user. In this regard, the pin wheels can be prepackaged in a slotted holder wherein the hubs are supported in vertical slots so that the pin wheels are positioned vertically with the their through-bores horizontal and accessible to receive the axial portions of the arm members of the pin wheel release mechanism. Once attached to the handle, the pin wheels can be lifted from the slotted holder. FIGS. 6a and 6b are side and end views of a pin wheel holder according to one embodiment of the present invention. As depicted in FIGS. 6a and 6b, the holder 27 has a width which is narrower that the width of the hubs 10 of the pin wheels 3. Pairs of aligned slots 28 are provided in the upper sides of the holder 27. The slots 28 have a width which is equal to or slightly larger than the diameter of the hubs 10. The slots 28 should have a depth which is at least equal to the radius of the hubs 10. FIG. 6a depicts three pin wheels 3 in holder 27 (pins are not shown). It is to be understood that the holder 28 could be sized to hold more than three pin wheels.

The pin wheels can be likewise easily released and discarded by providing a container with a slotted opening on an upper surface thereof. While attached to the handle, a pin wheel can be positioned or inserted in the slotted opening of the container prior to manipulating the pin wheel release mechanism. Once the pin wheel release mechanism is manipulated or slid so that the arm members move to their open position, the pin wheel can be pushed off the axial portions of the arm members by moving the handle in a direction perpendicular to the slot in the container. As the pin wheel drops off the handle it falls into the container. The slotted opening can be rectangular with a width large enough to receive the pin wheel. Otherwise the slotted opening can have a shape that is complementary to the cross section of the pin wheel (see FIG. 5).

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

I claim:

1. A device for testing the pain sensitivity of the skin of a patient which comprises:

a handle;

a pair of pivotable arm members extending from said handle;

a pin wheel releasably held between said pair of pivotable arm members; and a release mechanism within said handle for pivoting said arm members between an open and closed position, wherein said pin wheel is rotatably held by said pair of arm members in said closed position and released from said pair of arm members in said open position.

2. A device for testing the pain sensitivity of the skin of a patient according to claim 1, wherein said arm members include opposed axial portions which are received in said pin wheel to rotatable hold said pin wheel.

3. A device for testing the pain sensitivity of the skin of a patient according to claim 2 wherein said pin wheel includes a central hub having a through-bore therein which through-bore receives said opposed axial portions of said arm members.

4. A device for testing the pain sensitivity of the skin of a patient according to claim 1, wherein the release mechanism includes a pin wheel release lever which extends through a slot formed in said handle, and movement of said pin wheel release lever causes said pair of pivotable arm members to move between said open positions.

5. A device for testing the pain sensitivity of the skin of a patient according to claim 4, wherein said release mechanism includes a spring member which biases said pair of pivotable arm members in said closed position.

6. A device for testing the pain sensitivity of the skin of a patient according to claim 4, wherein said release mechanism includes a sliding member which includes a cam projection which cooperates with opposed cam surface provided on said pair of pivotal arm members.

7. A device for testing the pain sensitivity of the skin of a patient according to claim 6, wherein said release mechanism includes a spring member which biases said sliding member so that said pair of pivotable arm members is normally held in said closed position.

8. A device for testing the pain sensitivity of the skin of a patient according to claim 1, wherein said pin wheel includes a wheel and a plurality of pins which extend outwardly from a peripheral surface of said wheel.

9. A device for testing the pain sensitivity of the skin of a patient according to claim 8, wherein said pins and said wheel are integral.

10. A device for testing the pain sensitivity of the skin of a patient according to claim 9, wherein said pins and said wheel are made from a plastic.

11. A device for testing the pain sensitivity of the skin of a patient according to claim 9, wherein said pins and said wheel are made from a sterilizable material.

12. A device for testing the pain sensitivity of the skin of a patient according to claim 1, in combination with a plurality of pin wheels, wherein each of said plurality of pin wheels are disposable and held in a container so that they can be received by said pivotable arm members and removed from said container without being directly contacted by an operator of the device.

13. A device for testing the pain sensitivity of the skin of a patient according to claim 12, wherein each of said plurality of pin wheels includes a central hub which has opposite ends which are received in supporting slots in said container.

14. A device for testing the pain sensitivity of the skin of a patient according to claim 13, in combination with a container having a slot for receiving said pin wheels after use, said slot having a width equal to or greater than a width of said pin wheels and a length equal to or greater than a diameter of said pin wheels.

15. A method of testing the pain sensitivity of the skin of a patient which comprises:

providing a handle having a a pair of pivotable arm members extending from said handle, said pair of pivotable arm members including opposed axial portions, and a release mechanism within said handle for pivoting said arm members between an open and closed position, wherein said pin wheel is rotatably held by said pair of arm members in said closed position and released from said pair of arm members in said open position;

providing at least one pin wheel having a central hub with a through-bore extending through said hub;

moving said pair of pivotable arms into said open position and aligning said opposed axial portions with the through-bore in said pin wheel hub;

moving said pair of arm members into said closed position so that said opposed axial portions are received in said through-bore in said pin wheel hub to rotatably hold said pin wheel; and rolling said pin wheel across the skin of a patient to test pain sensitivity of the skin of the patient.

16. A method of testing the pain sensitivity of the skin of a patient according to claim 15, wherein said at least one pin wheel is held in a container so as to received by said pivotable arm members and removed from said container without being directly contacted by an operator of the device.

17. A method of testing the pain sensitivity of the skin of a patient according to claim 16, further comprising disposing of said used pin wheel by:

providing a waste container having a slot in an upper surface thereof;

positioning said used pin wheel in said slot; and moving said pair of arm members into said open position so that said opposed axial portions are removed from said through-bore in said pin wheel hub and said pin wheel drops into said waste container through said slot.

* * * * *